US00PP34863P2

(12) United States Plant Patent
von Tubeuf

(10) Patent No.: US PP34,863 P2
(45) Date of Patent: Dec. 20, 2022

(54) ***LOBELIA* PLANT NAMED 'KLELE21019'**

(50) Latin Name: *Lobelia erinus*
Varietal Denomination: KLELE21019

(71) Applicant: Klemm+Sohn GmbH & Co. KG, Stuttgart (DE)

(72) Inventor: Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/830,170

(22) Filed: Jun. 1, 2022

(51) Int. Cl.
*A01H 5/02* (2018.01)
*A01H 6/26* (2018.01)

(52) U.S. Cl.
USPC ..... Plt./451

(58) Field of Classification Search
USPC ..... Plt./263.1, 451
See application file for complete search history.

(56) References Cited

U.S. PATENT DOCUMENTS

PP12,708 P2 * 6/2002 Westhoff ..... A01H 5/02
Plt./451

* cited by examiner

*Primary Examiner* — Karen M Redden
(74) *Attorney, Agent, or Firm* — Weatherly IP Solutions, LLC; Barbara Campbell

(57) ABSTRACT

A new *Lobelia* plant particularly distinguished by white flowers and a semi-upright and freely-branching habit, is disclosed.

1 Drawing Sheet

Genus and species: *Lobelia erinus.*
Variety denomination: 'KLELE21019'.

BACKGROUND OF THE NEW PLANT

The present invention comprises a new and distinct variety of *Lobelia*, botanically known as *Lobelia erinus*, and hereinafter referred to by the variety name 'KLELE21019'. 'KLELE21019' originated from a controlled cross-pollination in June 2014 in Stuttgart, Germany between the proprietary female *Lobelia* variety 'LE-2013-0014' (unpatented) and the proprietary male *Lobelia* variety 'LE-2010-0044' (unpatented).

The seeds from the cross were sown and plants were grown in a greenhouse for evaluation, where an individual plant designated 'KLELE21019' was selected from the group. 'KLELE21019' was first vegetatively propagated via apical vegetative cuttings. 'KLELE21019' was found to reproduce true to type in successive generations of asexual propagation via apical vegetative cuttings.

SUMMARY

The following are the most outstanding and distinguishing characteristics of this new variety when grown under normal horticultural practices in Stuttgart, Germany.

1. White flowers; and
2. A semi-upright and freely branching habit.

DESCRIPTION OF THE PHOTOGRAPH

This new *Lobelia* plant is illustrated by the accompanying photograph which shows the plant's overall plant habit including form, foliage, and flowers. The photograph is of a 3-month-old plant grown in a greenhouse in Stuttgart, Germany in November 2021. The colors shown are as true as can be reasonably obtained by conventional photographic procedures.

DESCRIPTION OF THE NEW VARIETY

The following detailed descriptions set forth the distinctive characteristics of 'KLELE21019'. The data which define these characteristics were collected from asexual reproductions carried out in Stuttgart, Germany. Data was collected on 8-week-old plants grown in a greenhouse in Stuttgart, Germany in April 2022. Color references are to The R.H.S. Colour Chart of The Royal Horticultural Society of London (R.H.S.), 5$^{th}$ edition (2007), unless otherwise noted.

Classification:
- *Family.*—Campanulaceae.
- *Botanical.—Lobelia erinus.*
- *Common.—Lobelia.*
- *Designation.*—'KLELE21019'.

Parentage:
- *Female parent.*—The proprietary female *Lobelia* variety 'LE-2013-0014' (unpatented).
- *Male parent.*—The proprietary male *Lobelia* variety 'LE-2010-0044' (unpatented).

Growth:
- *Growth and branching habit.*—Semi-upright, freely branching.
- *Form.*—Triangular.
- *Height (measured from the top of the soil including any flowers).*—12.0 cm.
- *Width (horizontal plant diameter, including any flowers).*—18.0 cm.
- *Time to produce a finished flowering plant.*—7 weeks.
- *Outdoor plant performance.*—Very good.
- *Time to initiate roots.*—2 to 3 weeks.

*Root description*.—Fine, white roots, freely branching, and dense.

Leaves:

*Arrangement*.—Alternate.

*Color*.—Immature leaf: Upper surface: RHS 143B (Green). Lower surface: Closest to RHS 138B (Green). Mature leaf: Upper surface: RHS 137B (Green). Lower surface: RHS 138B (Green).

*Length*.—3.0 cm to 4.0 cm.

*Width*.—1.5 cm to 2.5 cm.

*Shape*.—Elliptic.

*Margin*.—Sinuate.

*Apex*.—Obtuse.

*Base*.—Attenuate.

*Texture*.—Upper surface is slightly haired, while the lower surface is smooth.

*Venation*.—Pinnate.

*Venation color*.—Upper surface: RHS 139D (Green). Lower surface: RHS 139B (Green).

Stems:

*Length*.—6.0 cm to 10.0 cm.

*Diameter*.—0.2 cm.

*Internode length*.—1.0 cm to 2.0 cm.

*Texture*.—Slightly haired.

*Stem anthocyanin*.—Absent.

*Stem color*.—RHS 143A (Green).

*Peduncle*.—Length: 3.0 cm to 4.0 cm. Diameter: 0.05 cm. Texture: Smooth. Color: RHS 137C (Green).

Flower buds:

*Shape*.—Inverse drop-shaped.

*Diameter*.—0.25 cm to 0.3 cm.

*Length*.—0.8 cm to 1.0 cm.

*Color*.—Between RHS 154D (Yellow-Green) and RHS 1D (Green-Yellow).

Inflorescence:

*Blooming habit*.—Continuous.

*Lastingness of individual blooms on plant*.—Approximately 2 weeks.

*Fragrance*.—Absent.

*Inflorescence type*.—Raceme.

*Quantity of flowers and buds per flowering branch*.—5 to 8.

Flowers:

*Flower diameter* (*horizontal*).—2.3 cm.

*Flower height* (*vertical*).—0.7 cm.

*Mature flower*.—Upper lobe: Color, upper surface: RHS NN155D (White). Length: 0.7 cm. Width: 0.25 cm. Shape: Spatulate. Apex: Mucronate. Margin: Entire. Texture (both upper and lower surfaces): Smooth. Lower lobe: Color, upper surface: RHS NN155D (White). Color, lower surface: RHS NN155D (White). Length: 1.0 cm. Width: 0.8 cm. Shape: Orbicular. Apex: Mucronate. Margin: Entire. Texture (both upper and lower surfaces): Smooth.

*Corolla tube*.—Color inside: RHS NN155D (White) with 2 spots between RHS 149A (Yellow-Green) and RHS 150A (Yellow-Green). Color outside: RHS NN155D (White). Tube length: 0.8 cm. Diameter: 0.8 cm.

*Calyx*.—Length: 0.8 cm (can include an additional 0.2 cm for the fused part). Diameter: 0.2 cm (measured at the fusion point). Shape: Composed of 5 narrowly triangular single leaflets forming a star shaped calyx fused in the lower quarter. Apex: Narrowly acute. Texture: Smooth. Color: RHS N137C (Green).

Reproductive organs:

*Stamens*.—Quantity per flower: 5. Filament length: 0.7 cm. Filament color: RHS NN155D (White). Anther length: 0.8 cm. Anther width: 0.1 cm. Anther color: RHS 161C (Greyed-Yellow). Pollen color: RHS 11C (Yellow). Pollen amount: Sparse.

*Pistils*.—Stigma shape: Circular. Stigma, general color: Grey. Style length: 0.8 cm. Style color: RHS 145C (Yellow-Green). Ovary color: RHS 145B (Yellow-Green). Ovary shape: Round.

Fruit and seed set: Fruit and seed set not observed to date.

Disease and pest/insect resistance: No disease and pest/insect resistance observed to date.

COMPARISON WITH PARENTAL LINES AND KNOWN VARIETY

'KLELE21019' can be distinguished from its parents as described in Table 1.

TABLE 1

Comparison with Parental Lines

| Characteristic | 'KLELE21019' | Female Parent 'LE-2013-0014' | Male Parent 'LE-2010-0044' |
|---|---|---|---|
| Flower color | White | Lavender-pink | Dark-blue |
| Foliage color | Green | Green | Greyed-green |
| Habit | Semi-upright | Upright | Semi-upright |

'KLELE21019' is most similar to the commercial *Lobelia* variety HOT 'White' ('Weslowhite'; U.S. Plant Pat. No. 16,295). Differences between the varieties are described in Table 2.

TABLE 2

Comparison with Similar Variety

| Characteristic | 'KLELE21019' | HOT 'White' |
|---|---|---|
| Flower size | Larger than HOT 'White' | Smaller than 'KLELE21019' |
| Foliage color | Green | Greyed-green |

I claim:

1. A new and distinct variety of *Lobelia* plant designated 'KLELE21019' as illustrated and described herein.

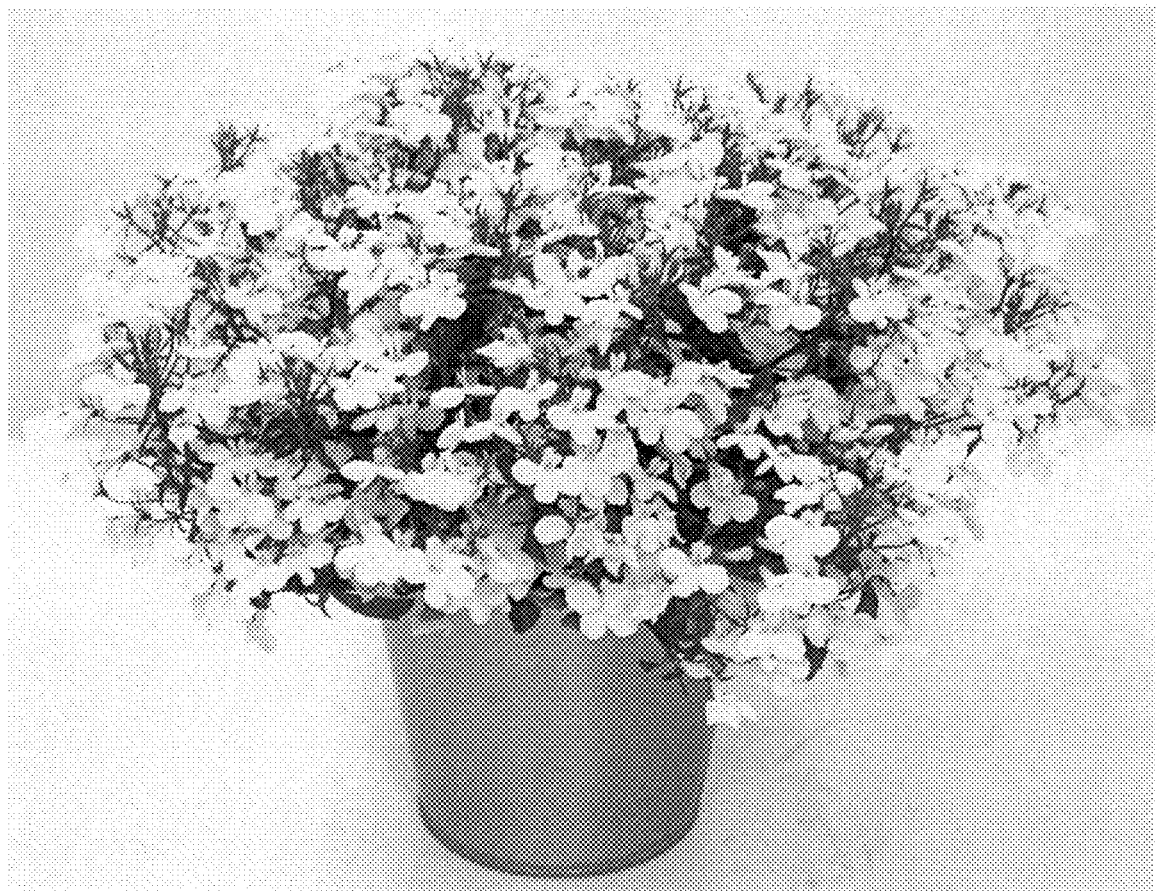

* * * * *